(12) United States Patent
Ishii et al.

(10) Patent No.: US 6,201,156 B1
(45) Date of Patent: Mar. 13, 2001

(54) METHOD FOR PRODUCTION OF ALDEHYDES

(75) Inventors: Yasutaka Ishii, Takatsuki; Tatsuya Nakano, Himeji, both of (JP)

(73) Assignee: Daicel Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/394,101

(22) Filed: Sep. 13, 1999

(51) Int. Cl.$^7$ ................................................ C07C 47/542
(52) U.S. Cl. ......................... 568/436; 568/426; 568/449; 568/483; 568/485
(58) Field of Search .................... 568/426, 436, 568/449, 469.7, 483, 485

(56) References Cited

U.S. PATENT DOCUMENTS

| | | | |
|---|---|---|---|
| 6,023,000 | * | 2/2000 | Fritz-Langhals et al. ........... 568/320 |
| 6,069,282 | * | 5/2000 | Fritz-Langhals et al. ........... 568/320 |

OTHER PUBLICATIONS

Satoshi Sakaguchi, Masahiro Eikawa and Yasutaka Ishii; "N–Hydroxyphthalimide (NHPI)–Catlayzed Reaction of Adamantane Under Nitric Oxide Atmosphere"; 1997; Tetrahedron Letters, vol. 38. No. 40, pp. 7075–7078.

Masahiro Eikawa, Satoshi Sakaguchi, and Yasutaka Ishii; "A New Approach for Oxygenation Using Nitric Oxide under the Influence of N–Hydroxyphthalimide"; 1999; J. Org. Chem. 64, pp. 4676–4679.

Yasutaka Ishii, Satoshi Sakaguchi and Takahiro Iwahama; "Development of Novel Aerobic Oxidation Method using N–Hydroxphthalimide as Catalyst"; 1999; pp. 38–48; Yuki Gosei Kagaku Kyokaishi (1999), 57(1), 24–34.

\* cited by examiner

Primary Examiner—Sreeni Padmanabhan
(74) Attorney, Agent, or Firm—Birch, Stewart, Kolasch & Birch, LLP

(57) ABSTRACT

An ether of the following formula (2):

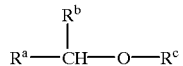

(2)

(wherein $R^a$ is a hydrogen atom, a hydrocarbon group or a heterocyclic group, $R_b$ is a hydrogen atom, a hydroxyl group or a substituted oxy group, and $R^c$ is a hydrocarbon group or a heterocyclic group; $R^a$ and $R^c$ may be combined to form a ring with the adjacent carbon atom and oxygen atom) is reacted with nitrogen monoxide in the presence of a catalyst composed of an imide compound of the following formula (1):

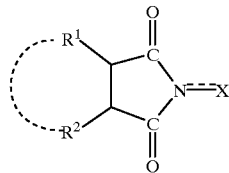

(1)

(wherein each of $R^1$ and $R^2$ is, identical to or different from each other, a hydrogen atom, a halogen atom, an alkyl group, an aryl group, a cycloalkyl group, a hydroxyl group, an alkoxy group, a carboxyl group, an alkoxycarbonyl group, or an acyl group; $R^1$ and $R^2$ may be combined to form a double bond, or an aromatic or nonaromatic ring; X is an oxygen atom or a hydroxyl group; and one or two N-substituted cyclic imido groups indicated in the formula (1) may further be formed on $R^1$, $R^2$, or on the double bond or aromatic or nonaromatic ring formed together by $R^1$ and $R^2$) to give an aldehyde of the following formula (3):

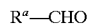

(3)

(wherein $R^a$ has the same meaning as defined above).

13 Claims, No Drawings

METHOD FOR PRODUCTION OF ALDEHYDES

TECHNICAL FIELD OF THE INVENTION

The present invention relates to a process for the production of aldehydes. More particularly, it relates to a process for the production of corresponding aldehydes from ethers.

BACKGROUND ART

Aldehyde compounds are important compounds as, for example, pharmaceuticals, agricultural chemicals, perfumes, dyes, and organic intermediates.

As processes for obtaining aldehydes from ethers are known processes using, for example, a peroxide, lead tetraacetate, or copper nitrate as an oxidizing agent. These processes, however, require the use of dangerous reagents and/or metallic compounds in large amounts, and are therefore disadvantageous in handling property and cost efficiency.

Tetrahedron Lett., 1997, 7075 reports that when adamantane is reacted with nitrogen monoxide using N-hydroxyphthalimide as a catalyst, as in the present invention, Ritter reaction proceeds to give corresponding amides. This report lacks, however, a description of a reaction between ethers and nitrogen monoxide.

SUMMARY OF THE INVENTION

Accordingly, it is an object of the present invention to provide a process for the production of corresponding aldehydes from ethers in high yields with ease.

After intensive investigations to achieve the above object, the present inventors found that a reaction of ethers with nitrogen monoxide in the presence of a specific catalyst gives corresponding aldehydes in high yields. The present invention has been accomplished based on the above finding.

To be more specific, the invention provides, in an aspect, a process for the production of aldehydes, the process including the step of: reacting an ether represented by the following formula (2):

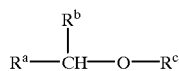
(2)

(wherein $R^a$ is a hydrogen atom, a hydrocarbon group or a heterocyclic group, $R^b$ is a hydrogen atom, a hydroxyl group or a substituted oxy group, and $R^c$ is a hydrocarbon group or a heterocyclic group; $R^a$ and $R^c$ may be combined to form a ring with the adjacent carbon atom and oxygen atom)

with nitrogen monoxide in the presence of a catalyst being composed of an imide compound represented by the following formula (1):

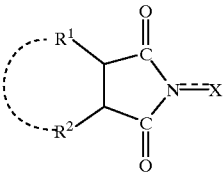
(1)

(wherein each of $R^1$ and $R^2$ is, identical to or different from each other, a hydrogen atom, a halogen atom, an alkyl group, an aryl group, a cycloalkyl group, a hydroxyl group, an alkoxy group, a carboxyl group, an alkoxycarbonyl group, or an acyl group; $R^1$ and $R^2$ may be combined to form a double bond, or an aromatic or nonaromatic ring; X is an oxygen atom or a hydroxyl group; and one or two N-substituted cyclic imido groups indicated in the formula (1) may further be formed on the aforementioned $R^1$, $R^2$, or on the double bond or aromatic or nonaromatic ring formed together by $R^1$ and $R^2$)

to give an aldehyde represented by the following formula (3):

$R^a$—CHO (3)

(wherein $R^a$ has the same meaning as defined above)

The invention provides, in another aspect, a process for the production of aldehydes, the process including the step of:

reacting an ether represented by the following formula (2a)

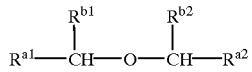
(2a)

(wherein each of $R^{a1}$ and $R^{a2}$ is, identical to or different from each other, a hydrogen atom, a hydrocarbon group or a heterocyclic group; and each of $R^{b1}$ and $R^{b2}$ is, identical to or different from each other, a hydrogen atom, a hydroxyl group or a substituted oxy group; $R^{a1}$ and $R^{a2}$ may be combined to form a ring with the adjacent carbon atom and oxygen atom)

with nitrogen monoxide in the presence of a catalyst being composed of the imide compound represented by the formula (1) to give an aldehyde represented by the following formula (3a-1) and/or (3a-2):

$R^{a1}$—CHO (3a-1)

$R^{a2}$—CHO (3a-2)

(wherein each of $R^{a1}$ and $R^{a2}$ is, identical to or different from each other, a hydrogen atom, a hydrocarbon group or a heterocyclic group; $R^{a1}$ and $R^{a2}$ may be combined with each other).

In the inventive processes, the amount of the nitrogen monoxide may for example be equal to or more than 5 moles relative to 1 mole of the ether, a substrate.

DETAILED DESCRIPTION OF THE INVENTION

According to the invention, the imide compound represented by the formula (1) is used as a catalyst. Of the substituents $R^1$ and $R^2$ in the formula (1), the halogen atom includes iodine, bromine, chlorine and fluorine. The alkyl group includes, for instance, methyl, ethyl, propyl, isopropyl, butyl, isobutyl, s-butyl, t-butyl, pentyl, hexyl, heptyl, octyl, and decyl groups, and other straight- or branched-chain alkyl groups each having about 1 to 10 carbon atoms. As preferred alkyl groups, there may be mentioned, for instance, alkyl groups each having about 1 to 6 carbon atoms, and more preferably lower alkyl groups each having about 1 to 4 carbon atoms.

The aryl group includes phenyl, and naphthyl groups, for example; and the cycloalkyl group includes cyclopentyl, and cyclohexyl groups. As the alkoxy group, there may be mentioned, for example, methoxy, ethoxy, propoxy, isopropoxy, butoxy, isobutoxy, t-butoxy, pentyloxy and hexyloxy groups, and other alkoxy groups each having about 1 to 10 carbon atoms, preferably about 1 to 6 carbon atoms, of which lower alkoxy groups each having about 1 to 4 carbon atoms are especially preferred.

Examples of the alkoxycarbonyl group include methoxycarbonyl, ethoxycarbonyl, propoxycarbonyl, isopropoxycarbonyl, butoxycarbonyl, isobutoxycarbonyl, t-butoxycarbonyl, pentyloxycarbonyl and hexyloxycarbonyl groups, and other alkoxycarbonyl groups each having about 1 to 10 carbon atoms in the alkoxy moiety. Preferred alkoxycarbonyl groups include alkoxycarbonyl groups each having about 1 to 6 carbon atoms in the alkoxy moiety, and especially lower alkoxycarbonyl groups each having about 1 to 4 carbon atoms in the alkoxy moiety. As the illustrative acyl group, there maybe mentioned formyl, acetyl, propionyl, butyryl, isobutyryl, valeryl, isovaleryl, and pivaloyl groups, and other acyl groups each having about 1 to 6 carbon atoms.

The substituents $R^1$ and $R^2$ may be identical to or different from each other. The substituents $R^1$ and $R^2$ in the formula (1) may be combined to form a double bond, or an aromatic or nonaromatic ring. The preferred aromatic or nonaromatic ring is a 5- to 12-membered ring, and especially a 6- to 10-membered ring. It may be a heterocyclic ring or condensed heterocyclic ring, but it is often a hydrocarbon ring. Such rings include, for example, nonaromatic alicyclic rings (e.g., cyclohexane ring and other cycloalkane rings which may have a substituent, cyclohexene ring and other cycloalkene rings which may have a substituent), nonaromatic bridged rings (e.g., 5-norbornene ring and other bridged hydrocarbon rings which may have a substituent), benzene ring, naphthalene ring and other aromatic rings (including condensed rings) which may have a substituent. The ring is composed of an aromatic ring in many instances. The ring may have a substituent such as an alkyl group, a haloalkyl group, a hydroxyl group, an alkoxy group, a carboxyl group, an alkoxycarbonyl group, an acyl group, a nitro group, a cyano group, an amino group, or a halogen atom.

In the formula (1), X represents an oxygen atom or a hydroxyl group, and the bond between the nitrogen atom N and X is a single bond or a double bond.

On $R^1$, $R^2$, or on the double bond or aromatic or nonaromatic ring formed together by $R^1$ and $R^2$, one or two N-substituted cyclic imido groups indicated in the formula (1) may further be formed. By way of illustration, when $R^1$ or $R^2$ is an alkyl group having 2 or more carbon atoms, the N-substituted cyclic imido group may be formed together with adjacent two carbon atoms constituting the alkyl group. Likewise, when $R^1$ and $R^2$ are combined to form a double bond, the N-substituted cyclic imido group may be formed together with the double bond. In case that $R^1$ and $R^2$ are combined to form an aromatic or nonaromatic ring, the N-substituted cyclic imido group may be formed with adjacent two carbon atoms constituting the aforementioned ring.

Preferred imide compounds include compounds represented by the following formulas:

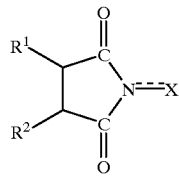

(1a)

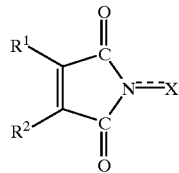

(1b)

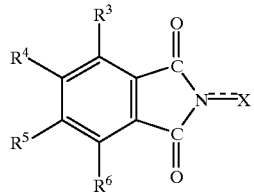

(1c)

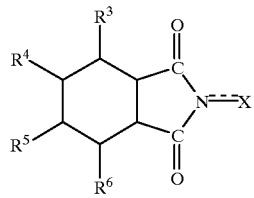

(1d)

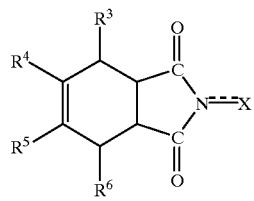

(1e)

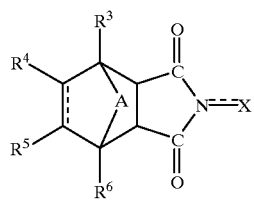

(1f)

(wherein each of $R^3$ to $R^6$ is, identical to or different from each other, a hydrogen atom, an alkyl group, a haloalkyl group, a hydroxyl group, an alkoxy group, a carboxyl group, an alkoxycarbonyl group, an acyl group, a nitro group, a cyano group, an amino group, or a halogen atom; or, of $R^3$ to $R^6$, adjacent groups may be combined to form an aromatic or nonaromatic ring; in the formula (1f), A represents a methylene group or an oxygen atom, and $R^1$ and $R^2$ have the same meanings as defined above; and one or two N-substituted cyclic imido groups indicated in the formula (1c) may further be formed on the benzene ring in the formula (1c))

In the substituents $R^3$ to $R^6$, the alkyl group includes similar alkyl groups to those exemplified above, especially alkyl groups having about 1 to 6 carbon atoms. The haloalkyl group includes trifluoromethyl group and other haloalkyl groups each having about 1 to 4 carbon atoms, and the alkoxy group includes similar alkoxy groups to those mentioned above, and especially lower alkoxy groups each having about 1 to 4 carbon atoms. The alkoxycarbonyl group includes similar alkoxycarbonyl groups to those described above, particularly lower alkoxycarbonyl groups each having about 1 to 4 carbon atoms in the alkoxy moiety. As the acyl group, there may be mentioned similar acyl groups to those described above, especially acyl groups each having about 1 to 6 carbon atoms, and the illustrative halogen atoms include fluorine, chlorine and bromine atoms. The substituents $R^3$ to $R^5$ are each a hydrogen atom, a lower alkyl group having about 1 to 4 carbon atoms, a carboxyl group, a nitro group, or a halogen atom in many instances. The ring formed together by $R^3$ to $R^6$ includes similar rings to the aforementioned rings which are formed together by $R^1$ and $R^2$. Among them, aromatic or nonaromatic 5- to 12-membered rings are particularly preferred.

As illustrative preferred imide compounds, there may be mentioned N-hydroxysuccinimide, N-hydroxymaleimide, N-hydroxyhexahydrophthalimide, N,N'-dihydroxycyclohexanetetracarboximide, N-hydroxyphthalimide, N-hydroxytetrabromophthalimide, N-hydroxytetrachlorophthalimide, N-hydroxychlorendimide, N-hydroxyhimimide, N-hydroxytrimellitimide, N,N'-dihydroxypyromellitimide, and N,N'-dihydroxynaphthalenetetracarboximide.

The imide compounds represented by the formula (1) can be prepared by a conventional imidation reaction, for example by a process in which a corresponding acid anhydride is reacted with hydroxylamine, $NH_2OH$, and the acid anhydride group is ring-opened and then is ring-closed to give an imide.

Such acid anhydrides include succinic anhydride, maleic anhydride and other saturated or unsaturated aliphatic dicarboxylic anhydrides, tetrahydrophthalic anhydride, hexahydrophthalic anhydride (1,2-cyclohexanedicarboxylic anhydride), 1,2,3,4-cyclohexanetetracarboxylic 1,2-dianhydride, and other saturated or unsaturated nonaromatic cyclic polycarboxylic anhydrides (alicyclicpolycarboxylicanhydrides), HET anhydride (chlorendic anhydride), himic anhydride, and other bridged polycarboxylic anhydrides (alicyclic polycarboxylic anhydrides), phthalic anhydride, tetrabromophthalic anhydride, tetrachlorophthalic anhydride nitrophthalic anhydride, trimellitic anhydride, methylcyclohexenetricarboxylic anhydride, pyromellitic anhydride, mellitic anhydride, 1,8;4,5-naphthalenetetracarboxylic dianhydride, and other aromatic polycarboxylic anhydrides.

Typically preferred imide compounds include N-hydroxyimide compounds derived from alicyclic polycarboxylic anhydrides or aromatic polycarboxylic anhydrides, of which N-hydroxyphthalimide and other N-hydroxyimide compounds derived from aromatic polycarboxylic anhydrides are especially preferred.

Each of the imide compounds represented by the formula (1) can be used singly or in combination. The imide compounds can be used as being supported by carriers. As such carriers, activated carbon, zeolite, silica, silica-alumina, bentonite and other porous carries are frequently employed. When the imide compound is supported on a carrier, its proportion falls in the range from about 0.1 to 50 parts by weight, preferably from about 0.5 to 30 parts by weight, and more preferably from about 1 to 20 parts by weight relative to 100 parts by weight of the carrier.

The amount of the imide compound of the formula (1) can be selected within a wide range, and is, for example, from about 0.001 to 1 mole, preferably from about 0.001 to 0.5 mole, and more preferably from about 0.01 to 0.30 mole relative to 1 mole of the ether. It is frequently used in an amount from about 0.01 to 0.25 mole relative to 1 mole of the ether.

In the invention, a co-catalytic component can be added in addition to the imide compound, but co-existence of a metal or metallic compound is liable to deteriorate the yield of the aldehyde.

According to the invention, ethers are used as reactants (substrates). In the ethers of the formula (2) and formula (2a), the hydrocarbon groups in $R^a$, $R^c$, $R^{a1}$ and $R^{a2}$ include aliphatic hydrocarbon groups, alicyclic hydrocarbon groups and aromatic hydrocarbon groups. As such aliphatic hydrocarbon groups, there may be mentioned, for example, methyl, ethyl, propyl, isopropyl, butyl, isobutyl, s-butyl, t-butyl, pentyl, hexyl, octyl and decyl groups, and other alkyl groups each having about 1 to 15 (preferably 1 to 10) carbon atoms; vinyl and 2-propenyl groups, and other alkenyl groups each having about 2 to 15 (preferably 2 to 10) carbon atoms; ethynyl and propynyl groups, and other alkynyl groups each having about 2 to 15 (preferably 2 to 10) carbon atoms.

The illustrative alicyclic hydrocarbon groups include cyclopropyl, cyclobutyl, cyclopentyl, cyclohexyl, cyclooctyl and cyclohexenyl groups, and other cycloalkyl groups or cycloalkenyl groups each having about 3 to 15 (preferably 3 to 10) carbon atoms; and bridged carbocyclic groups. A benzene ring, cyclohexane ring, or another carbocyclic ring, a pyridine ring or another heterocyclic ring may be condensed to nonaromatic carbocyclic rings constituting the alicyclic hydrocarbon groups.

Examples of the aromatic hydrocarbon groups include phenyl and naphthyl groups. A cyclohexane ring, or another carbocyclic ring, a pyridine ring or another heterocyclic ring maybe condensed to aromatic rings constituting the aromatic hydrocarbon groups.

As examples of heterocyclic rings corresponding to the heterocyclic groups in $R^a$, $R^c$, $R^{a1}$ and $R^{a2}$, there may be mentioned furan, oxazole, isoxazole, thiophene, thiazole, isothiazole, thiadiazole, pyrrol, pyrazole, imidazole, triazole, pyridine, pyridazine, pyrimidine and pyrazine rings, and other 5- or 6-membered heterocyclic rings each having about 1 to 3 of at least one heteroatom selected from nitrogen, oxygen and sulfur atoms.

To the heterocyclic rings, a benzene ring, cyclohexane ring, or another carbocyclic ring, a pyridine ring or another heterocyclic ring may be condensed.

Rings formed by $R^a$ and $R^c$, or $R^{a1}$ and $R^{a2}$ together with the adjacent carbon atom and oxygen atom include, for instance, oxetane, 2,5-dihydrofuran, tetrahydrofuran, 3,6-dihydropyran, tetrahydropyran, dihydroxepin, tetrahydroxepin, oxepane, dihydroxocin, tetrahydroxocin, oxocane, 1,3,5,7-tetraoxocane, dihydroxonin, dioxane, dihydrodioxin, dihydroxathiin, tetrahydroxathiin, dihydroxazine and perhydroxazine rings, and other nonaromatic heterocyclic rings each having about 3 to 20 members (preferably 3 to 15 members, more preferably 4 to 10 members) and containing at least one oxygen atom. To the rings, abenzene ring, cyclohexane ring or another carbocyclic ring (e.g., aromatic or nonaromatic carbocyclic ring having about 3 to 15 members), or a pyridine ring or another heterocyclic ring (e.g., aromatic or nonaromatic heterocyclic ring having about 3 to 15 members) may be condensed. Such condensed rings formed by condensation with a carbocyclic ring or heterocyclic ring include, for example, coumaran, isocoumaran (phthalan), chroman, chromene, isochroman, irochromene, xanthene, benzoxazine, and 3,6,8-trioxabicyclo[3.2.2]nonane rings. When $R^a$ and $R^c$, or $R^{a1}$ and $R^{a2}$, are combined to form a ring together with the adjacent carbon atom and oxygen atom, the ethers of the formula (2) and formula (2a) constitute cyclic ethers.

The hydrocarbon groups, heterocyclic groups, and rings formed by $R^a$ and $R^c$, or $R^{a1}$ and $R^{a2}$, together with the adjacent carbon atom and oxygen atom may have a variety of substituents. Examples of such substituents include halogen atoms (iodine, bromine, chlorine and fluorine atoms), an oxo group, a hydroxyl group, a mercapto group, hydroxyalkyl groups (e.g., hydroxymethyl, 2-hydroxyethyl groups and other hydroxy-$C_{1-4}$ alkyl groups), substituted oxy groups [e.g., alkoxy groups (e.g., methoxy group and other $C_{1-4}$ alkoxy groups), aryloxy groups, acyloxy groups (e.g., acetoxy, benzoyloxy groups and other $C_{2-10}$ acyloxy groups)], substituted thio groups, a carboxyl group, substituted oxycarbonyl groups (e.g., methoxycarbonyl, ethoxycarbonyl, and hexyloxycarbonyl groups and other alkoxycarbonyl groups each having about 1 to 6, especially about 1 to 4, carbon atoms in the alkoxy moiety), substituted or unsubstituted carbamoyl groups, substituted or unsubstituted amino groups, a cyano group, a nitro group, alkylgroups (e.g., $C_{1-4}$ alkylgroups), alkenylgroups (e.g., $C_{2-4}$ alkenyl groups), alkynyl groups (e.g., $C_{2-4}$ alkynyl groups), cycloalkyl groups, cycloalkenyl groups, aryl groups (e.g., phenyl and naphthyl groups), aralkyl groups, and heterocyclic groups.

The substituted oxy groups in $R^b$, $R^{b1}$ and $R^{b2}$ include groups which can be converted into hydroxyl groups through water in a reaction system. As examples of such groups, there may be mentioned methoxy, ethoxy and isopropoxy groups, and other alkoxy groups (e.g., $C_{1-4}$ alkoxy groups); allyloxy group and other alkenyloxy groups (e.g., $C_{2-4}$ alkenyloxy groups); and acetoxy and benzoyloxy groups, and other acyloxy groups (e.g., $C_{2-10}$ acyloxy groups).

Of the ethers represented by the formula (2), preferred compounds include (i) compounds in which $R^a$ is a 1-alkenyl group (e.g., vinyl, 1-propenyl, or 1-butenyl group or another 1-$C_{2-15}$ alkenyl group), and (ii) compounds in which $R^a$ and $R^c$ together form, with the adjacent carbon atom and oxygen atom, a nonaromatic heterocyclic ring having about 3 to 20 members (preferably 3 to 15 members, more preferably 4 to 10 members), where a carbocyclic ring or heterocyclic ring may be condensed to the nonaromatic heterocyclic ring. As the above compounds (ii), particularly preferred are compounds each having a double bond or an aromatic ring in the adjacent position to a carbon atom bonding to an oxygen atom constituting an ether bond. In this connection, the compounds of the formula (2a) correspond to, of the compounds of the formula (2), compounds each having carbon-hydrogen bonds in both adjacent positions to an oxygen atom constituting an ether bond.

Especially preferred compounds as the substrates used in the invention are "benzyl ethers (including cyclic ethers)" each having an aromatic ring in the adjacent position to a carbon atom bonded to an oxygen atom constituting an ether ring.

Typical examples of the ethers used as reactants in the invention include dimethyl ether, diethyl ether, dipropyl ether, diisopropyl ether, dibutyl ether, diisobutyl ether, dipentyl ether, diisopentyl ether, dihexyl ether, diheptyl ether, 1-chloro-2-ethoxyethane, bis(2-chloroethyl) ether, 2-ethoxyethanol, 2,2'-oxydiethanol, 3,3'-oxydipropionic acid, and other di-$C_{1-15}$ alkyl ethers (preferably di-$C_{1-10}$ alkyl ethers) which may have a substituent; diallyl ether, and other di-$C_{2-15}$ alkenyl ethers (preferably, di-$C_{2-10}$ alkenyl ethers) which may have a substituent; ethyl methyl ether, 2-methoxypropane, methyl butyl ether, 2-methoxybutane, 2-methoxypentane, 1-ethoxypropane, 2-ethoxypropane, 1-ethoxybutane, 2-ethoxybutane, 1-ethoxypentane, 2-ethoxypentane, 2-methoxyethanol., and other asymmetric $C_{1-15}$ alkyl $C_{1-15}$ alkyl ethers (preferably, asymmetric $C_{1-10}$ alkyl $C_{1-10}$ alkenyl ethers) which may have a substituent; vinyl allyl ether, and other asymmetric $C_{2-15}$ alkenyl $C_{2-15}$, alkenyl ethers (preferably, asymmetric $C_{2-10}$ alkenyl $C_{2-10}$ alkenyl ethers) which may have a substituent; methyl vinyl ether, methyl allyl ether, ethyl allyl ether, ethoxyethylene, 3-ethoxypropylene, and other $C_{1-15}$ alkyl $C_{2-15}$ alkenyl ethers (preferably $C_{-1-10}$ alkyl $C_{2-10}$ alkenyl ethers) which may have a substituent; cyclopropyl ethyl ether, cyclopropyl propyl ether, cyclopropyl butyl ether, cyclobutyl ethyl ether, cyclobutyl propyl ether, cyclobutyl butyl ether, cyclopentyl ethyl ether, cyclopentyl propyl ether, cyclopentyl butyl ether, cyclohexyl ethyl ether, cyclohexyl propyl ether, cyclohexyl butyl ether, and other $C_{1-15}$ alkyl $C_{3-15}$ cycloalkyl ethers (preferably, $C_{1-10}$ cycloalkyl $C_{3-10}$ cycloalkyl ethers) which may have a substituent; allyl cyclohexyl ether, and other $C_{2-10}$ alkenyl $C_{3-15}$ cycloalkyl ethers (preferably, $C_{2-10}$ alkenyl $C_{3-10}$ cycloalkyl ethers) which may have a substituent; methyl phenyl ether (anisole), ethyl phenyl ether (phenetole), propyl phenyl ether, anethole, naphthyl methyl ether, naphthyl ethyl ether, tolyl ethyl ether, 2-methoxyphenol, eugenol, and other $C_{1-15}$ alkyl aryl ethers (preferably, $C_{1-10}$ alkyl aryl ethers) which may have a substituent; benzyl methyl ether, benzyl ethyl ether, benzyl propyl ether, and other $C_{1-15}$ alkyl aralkyl ethers (preferably, $C_{1-10}$ alkyl aralkyl ethers) which may have a substituent; allylphenyl ether, and other $C_{2-15}$ alkenyl aryl ethers (preferably $C_{2-10}$ alkenyl aryl ethers) which may have a substituent; allyl benzyl ether, and other $C_{2-15}$ alkenyl aralkyl ethers (preferably, $C_{2-10}$ alkenyl aralkyl ethers) which may have a substituent; 1,2-dimethoxyethane, diethylene glycol dimethyl ether, 3,6-dioxyoctane, p-dimethoxybenzene, p-diethoxybenzene, 1,1'-(ethylenedioxy)dibenzene, 4,4'-(ethylenedioxy)dibenzoic acid, and other chain polyethers each having a plurality of ether bonds, which may have a substituent; oxirane, oxetane, propylene oxide, 2,5-dihydrofuran, tetrahydrofuran, 2-methyltetrahydrofuran, 1,3,5,7-tetraoxocane, dioxane, coumaran, isocoumaran (phthalan), 1-hydroxyphthalan, phtahlide, chroman, chromene, isochroman, 1-hydroxyisochroman, isochromene, xanthene, benzoxazine, 3,6,8-trioxabicyclo[3.2.2]nonane, crownether, 1-oxaspiro[4.5]decane, tetrahydropyran-2-spirocyclohexane, and other cyclic ethers which may have a substituent.

By reacting any of these ethers with nitrogen monoxide in the presence of the imide compound, a carbon site adjacent to an oxygen atom constituting an ether bond is oxidized to yield a corresponding aldehyde with efficiency, even under mild conditions.

For example, oxidation of the ethers of the formula (2) gives the corresponding aldehydes of the formula (3) in high yields. In this procedure, a moiety containing the $R^c$ group is generally converted into $R^c$—OH or an aldehyde corresponding to this alcohol. When the ethers of the formula (2a)

are oxidized, two types of aldehydes represented by the formula (3a-1) and/or (3a-2) are formed, or if the compounds of the formula (2a) are cyclic ethers, dialdehydes (compounds where $R^{a1}$ and $R^{a2}$ are bonded with each other) are formed. In this connection, water in existence (byproduced) in a reaction system is supposed to be involved in the reaction.

As nitrogen monoxide to be used for the oxidation of the ethers, both pure nitrogen monoxide, and nitrogen monoxide diluted with nitrogen, helium, argon, carbon dioxide or another inert gas can be used. Nitrogen monoxide formed in the reaction system can also be employed. Contamination of oxygen in the reaction system deteriorates the selectivity of the reaction, and corresponding esters or lactones are liable to be formed. For instance, the use of phthalane as the substrate in the presence of oxygen in the reaction system increases byproduction of phthalide and deteriorates the yield of phthalaldehyde.

The amount of nitrogen monoxide is generally about 1 mole or more, for example, 3 moles or more relative to 1 mole of the ether, the substrate. The use of nitrogen monoxide in an amount of 5 moles or more (e.g., about 5 to 30 moles, preferably 5 to 20 moles), more preferably 6 moles or more (e.g., about 6 to 20 moles), and especially 8 moles or more (e.g., about 8 to 20 moles) markedly improves the yield of the aldehyde.

A reaction is generally carried out in an inert organic solvent. Such organic solvents include, but are not limited to, acetonitrile, propionitrile, benzonitrile, and other nitriles; formamide, acetamide, dimethylformamide (DMF), dimethylacetamide, and other amides; hexane, octane, and other aliphatic hydrocarbons; benzene, toluene and other aromatic hydrocarbons; chloroform, dichloromethane, dichloroethane, carbon tetrachloride, chlorobenzene, and other halogenated hydrocarbons; nitrobenzene, nitromethane, nitroethane, and other nitro compounds; ethyl acetate, butyl acetate, and other esters; and mixtures of these solvents. The substrate can be used as a reaction solvent by using the same in an excess amount. As the solvent, acetonitrile, and other nitriles, and other neutral solvents are employed in may instances. The use of acetic acid or another acidic solvent is liable to deteriorate the yield of the aldehyde.

A distinguishing feature of the inventive process is that an oxidation reaction can smoothly proceed even under comparatively mild conditions. The reaction temperature can be chosen within an adequate range depending on, for example, the species of the substrate, and is, for instance, about 0C to 300° C., preferably about 10° C. to 250° C., and more preferably about 20° C. to 200° C. The reaction is generally carried out at a temperature of about 30° C. to 150° C. The reaction can be carried out at atmospheric pressure or under pressure. The reaction time can adequately be selected within the range of, for example, about 30 minutes to 48 hours, preferably about 1 to 36 hours, and more preferably about 2 to 24 hours, according to the reaction temperature and pressure.

The reaction can be conduced only by allowing the substrate to come in contact with nitrogen monoxide in the presence of the aforementioned catalyst. It can be performed in a batch system, semi-batch system, continuous system or another conventional system, in the presence of, or under the flow of, nitrogen monoxide. After the completion of the reaction, reaction products can be isolated and purified with facility in a conventional manner including, for example, filtration, concentration, distillation, extraction, crystallization, recrystallization, column chromatography and other isolation means, or any combination of these isolation means.

According to the inventive process, aldehydes can be produced from corresponding ethers with facility and efficiency under mild conditions.

The invention will be further illustrated in detail with reference to several inventive examples and comparative examples below which are not directed to limiting the scope of the invention.

EXAMPLE 1

A mixture of 10 mmol of phthalan (isocoumaran), 1 mmol of N-hydroxyphthalimide (NHPI), and 5 ml of acetonitrile was stirred at 60° C. under a nitrogen monoxide atmosphere (1 atm) for 6 hours. Gas chromatographic analysis of products in the reaction mixture revealed that phthalan was converted, at a rate of 90%, into phthalaldehyde (yield: 80%), and phthalide (1-phthalanone) (yield: 7%).

EXAMPLE 2

The procedure of Example 1 was repeated, except that 10 mmol of 2,5-dihydrofuran was used instead of phthalan. As a result, 2,5-dihydrofuran was converted, at a rate of 77%, into butenedial (yield: 70%), and 2,5-dihydro-2-furanone (yield: 4%)

EXAMPLE 3

A mixture of 1 mmol of benzyl methyl ether, 0.1 mmol of N-hydroxyphthalimide, and 5 ml of acetonitrile was stirred at 60° C. under a nitrogen monoxide atmosphere (1 atm) for 5 hours. Gas chromatographic analysis of products in the reaction mixture revealed that benzyl methyl ether was converted, at a rate of 78%, into benzaldehyde (yield: 52%), and methyl benzoate (yield: 20%).

EXAMPLE 4

A mixture of 1 mmol of benzyl ethyl ether, 0.1 mmol of N-hydroxyphthalimide, and 5 ml of acetonitrile was stirred at 60° C. under a nitrogen monoxide atmosphere (1 atm) for 5 hours. Gas chromatographic analysis of products in the reaction mixture revealed that benzyl ethyl ether was converted, at a rate of 82%, into benzaldehyde (yield: 57%), and ethyl benzoate (yield: 18%).

EXAMPLE 5

To a mixture of 10 mmol of phthalan (isocoumaran), 1 mmol of N-hydroxyphthalimide, and 5 ml of acetonitrile was introduced 10 mmol of nitrogenmonoxide, and the resultantmixture was stirred at 60° C. for 8 hours. Isolation of products in the reaction mixture by column chromatography on a silica gel revealed that phthalan was converted, at a rate of 15%, into phthalaldehyde (yield: 1%), 1-hydroxyphthalan (yield: 3%), NHPI adduct (yield: 3%), and an acetamide compound (yield: 3%).

(Spectrum data of 1-hydroxyphthalan)
$^1$H-NMR (CDCl$_3$, 270 MHz) δ: 10.2 (s, 1H), 7.86–7.23 (m, 8H), 6.41 (s, 1H), 5.28 (m, 2H), 5.13–5.09 (m, 3H)

EXAMPLE 6

To a mixture of 10 mmol of phthalan (isocoumaran), 1 mmol of N-hydroxyphthalimide, and 5 ml of acetonitrile was introduced 60 mmol of nitrogenmonoxide, and the resultant mixture was stirred at 60° C. for 8 hours. Isolation of products in the reaction mixture by column chromatography on a silica gel revealed that phthalan was converted, at a rate of 95%, into phthalaldehyde (yield: 88%) and 1-hydroxyphthalan (yield: 3%).

EXAMPLE 7

To a mixture of 10 mmol of phthalan (isocoumaran), 1 mmol of N-hydroxyphthalimide, and 5 ml of acetonitrile was introduced 120 mmol of nitrogen monoxide, and the resultant mixture was stirred at 60° C. for 8 hours. Isolation of products in the reaction mixture by column chromatography on a silica gel revealed that phthalan was converted, at a rate of 99%, into phthalaldehyde (yield: 94%).

EXAMPLE 8

A total of 13 mmol of nitrogen monoxide was introduced into a mixture of 1 mmol of 1-hydroxyphthalan, 0.1 mmol of N-hydroxyphthalimide, and 5 ml of acetonitrile, and the resultant mixture was stirred at 60° C. for 2 hours. Isolation of products in the reaction mixture by column chromatography on a silica gel revealed that 1-hydroxyphthalane was converted, at a rate of 99%, into phthalaldehyde (yield: 95%).

EXAMPLE 9

A mixture of 1 mmol of 4-methoxymethyltoluene, 0.1 mmol of N-hydroxyphthalimide, and 5 ml of acetonitrile was stirred at 60° C. under a nitrogen monoxide atmosphere (1 atm) for 5 hours. Isolation of products in the reaction mixture by column chromatography on a silica gel revealed that p-tolualdehyde was produced in yield of 50% at a conversion rate from 4-methoxymethyltoluene of 56%.

EXAMPLE 10

The procedure of Example 9 was repeated, except that 1 mmol of 4-ethoxymethyltoluene was used instead of 4-methoxymethyltoluene. As a result, 4-ethoxymethyltoluene was converted, at a rate of 70%, into p-tolualdehyde in a yield of 60%.

EXAMPLE 11

The procedure of Example 9 was repeated, except that 1 mmol of 4-t-butoxymethyltoluene was used instead of 4-methoxymethyltoluene. As a result, 4-t-butoxymethyltoluene was converted, at a rate of 90%, into p-tolualdehyde (yield: 72%).

EXAMPLE 12

Except for using 1 mmol of t-butoxymethylbenzene instead of 4-methoxymethyltoluene, the procedure of Example 9was repeated to give benzaldehyde in yield of 70% at a conversion rate from t-butoxymethylbenzene of 80%.

EXAMPLE 13

The procedure of Example 9 was repeated, except that 1 mmol of 1-t-butoxymethyl-4-t-butylbenzene was used instead of 4-methoxymethyltoluene. As a result, 1-t-butoxymethyl-4-t-butylbenzene was converted, at a rate of 95%, into 4-t-butylbenzaldehyde in a yield of 84%.

EXAMPLE 14

By using 1 mmol of 1-t-butoxymethyl-4-chlorobenzene instead of 4-methoxymethyltoluene, a reaction was conducted in the same manner as in Example 9. As a result, 1-t-butoxymethyl-4-chlorobenzene was converted, at a rate of 83%, into 4-chlorobenzaldehyde (yield: 74%5)

EXAMPLE 15

The procedure of Example 9 was repeated, except that 1 mmol of 1-t-butoxymethylnaphthalene was used instead of 4-methoxymethyltoluene. As a result, 1-t-butoxymethylnaphthalene was converted, at a rate of 87%, into 1-naphthylaldehyde (yield: 80%).

EXAMPLE 16

The procedure of Example 9 was repeated, except that 1 mmol of 2-t-butoxymethyl-7-methylnaphthalene was used instead of 4-methoxymethyltoluene, to give 7-methyl-2-naphthylaldehyde in yield of 85% at a conversion rate from 2-t-butoxymethyl-7-methylnaphthalene of 93%.

(Spectrum data of 7-methyl-2-naphthylaldehyde)
$^1$H-NMR (CDCl$_3$, 270 MHz) δ: 9.99 (s, 1H), 8.07-7.35 (m, 6H), 2.42 (s, 3H)

EXAMPLE 17

Except for using 1 mmol of dibenzyl ether instead of 4-methoxymethyltoluene, the procedure of Example 9 was repeated. As a result, dibenzyl ether was converted, at a rate of 82%, into benzaldehyde (yield: 64%) and benzyl alcohol (yield: 30%).

EXAMPLE 18

Except for using 1 mmol of 1,3-bis(t-butoxymethyl) benzene instead of 4-methoxymethyltoluene, the procedure of Example 9 was repeated. As a result, 1,3-bis(t-butoxymethyl)benzene was converted, at a rate of 99%, into 1,3-benzenedicarbaldehyde (yield: 75%), and 3-t-butoxymethylbenzaldehyde (yield: 10%).

(Spectrum data of 3-t-butoxymethylbenzaldehyde)
$^1$H-NMR (CDCl$_3$, 270 MHz) δ: 10.6 (s, 1H), 8.46–7.45 (m, 4H), 4.51 (s, 2H), 1.31 (s, 9H)

EXAMPLE 19

The procedure of Example 9 was repeated, except that 1 mmol of 1,4-bis(methoxymethyl)benzene was used instead of 4-methoxymethyltoluene to give terephthalaldehyde (yield: 53%) and 4-methoxymethylbenzaldehyde (yield: 20%) at a conversion rate from 1,4-bis(methoxymethyl) benzene of 96%.

(Spectrum data of 4-methoxymethylbenzaldehyde)
$^1$H-NMR (CDCl$_3$, 270 MHz) δ: 8.79 (s, 1H), 6.66 (d, J=7.8 Hz, 2H), 6.29 (d, J=7.8 Hz, 2H), 3.33 (s, 2H), 2.23 (s, 3H);

What is claimed is:
1. A process for the production of aldehydes, said process comprising the step of:
reacting an ether represented by the following formula (2):

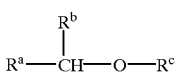

(2)

(wherein $R^a$ is a hydrogen atom, a hydrocarbon group or a heterocyclic group, $R^b$ is a hydrogen atom, a hydroxyl group or a substituted oxy group which can be converted into the hydroxyl group through water in a reaction system, and $R^c$ is a hydrocarbon group or a heterocyclic group; or $R^a$ and $R^c$ may be combined to form a ring with the adjacent carbon atom and oxygen atom)

with nitrogen monoxide in the presence of a catalyst being composed of an imide compound represented by the following formula (1):

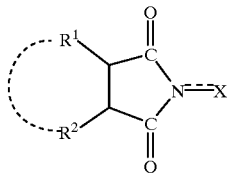

(1)

(wherein each of $R^1$ and $R^2$ is, identical to or different from each other, a hydrogen atom, a halogen atom, an alkyl group, an aryl group, a cycloalkyl group, a hydroxyl group, an alkoxy group, a carboxyl group, an alkoxycarbonyl group, or an acyl group, $R^1$ and $R^2$ may be combined to form a double bond, or an aromatic or nonaromatic ring; X is an oxygen atom or a hydroxyl group; and one or two N-substituted cyclic imido groups indicated in the formula (1) may further be formed on the aforementioned $R^1$, $R^2$, or on the double bond or aromatic or nonaromatic ring formed together by $R^1$ and R2)

to give an aldehyde represented by the following formula (3):

$$R^a\text{—CHO} \qquad (3)$$

(wherein $R^a$ has the same meaning as defined above.

2. A process for the production of aldehydes, said process comprising the step of:

reacting an ether represented by the following formula (2a):

(2a)

$$R^{a1}\text{—CH}(R^{b1})\text{—O—CH}(R^{b2})\text{—}R^{a2}$$

(wherein each of $R^{a1}$ and $R^{a2}$ is, identical to or different from each other, a hydrogen atom, a hydrocarbon group or a heterocyclic group; and each of $R^{b1}$ and $R^{b2}$ is, identical to or different from each other, a hydrogen atom, a hydroxyl group or a substituted oxy group; $R^{a1}$ and $R^{a2}$ may be combined to form a ring with the adjacent carbon atom and oxygen atom)

with nitrogen monoxide in the presence of a catalyst being composed of an imide compound represented by the following formula (1):

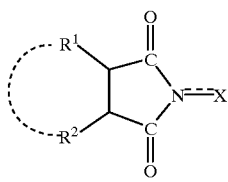

(1)

(wherein each of $R^1$ and $R^2$ is, identical to or different from each other, a hydrogen atom, a halogen atom, an alkyl group, an aryl group, a cycloalkyl group, a hydroxyl group, an alkoxy group, a carboxyl group, an alkoxycarbonyl group, or an acyl group, $R^1$ and $R^2$ may be combined to form a double bond, or an aromatic or nonaromatic ring; X is an oxygen atom or a hydroxyl group; and one or two N-substituted cyclic imido groups indicated in the formula (1) may further be formed on the aforementioned $R^1$, $R^2$, or on the double bond or aromatic or nonaromatic ring formed together by $R^1$ and $R^2$)

to give an aldehyde represented by the following formula (3a-1) and/or (3a-2):

$$R^{a1}\text{—CHO} \qquad (3a\text{-}1)$$

$$R^{a2}\text{—CHO} \qquad (3a\text{-}2)$$

(wherein each of $R^{a1}$ and $R^{a2}$ is, identical to or different from each other, a hydrogen atom, a hydrocarbon group or a heterocyclic group; $R^{a1}$ and $R^{a2}$ may be combined with each other to form a dialdehyde.

3. The process for the production of aldehydes according to either of claim 1 or 2, wherein nitrogen monoxide is used in a proportion of equal to or more than 5 moles relative to 1 mole of said ether.

4. The process for the production of aldehydes according to either of claim 1 or 2, wherein the substituents $R^1$ and $R^2$ in the formula (1) are combined to form a 5- to 12- membered aromatic or nonaromatic ring.

5. The process for the production of aldehydes according to claim 1, wherein the substituents of $R^a$ and $R^c$ in the formula (2) are independently aliphatic hydrocarbon groups having 1 to 15 carbon atoms, alicyclic hydrocarbon groups wherein a carbocyclic ring or heterocyclic ring may be condensed to a nonaromatic carbocyclic ring constituting the alicyclic hydrocarbon groups, aromatic hydrocarbon groups wherein a carbocyclic ring or heterocyclic ring may be condensed to an aromatic ring consisting the aromatic hydrocarbon groups, or heterocyclic groups each having a 5- or 6- membered heterocyclic ring 1 to 3 of at least one heteroatom selected from the group consisting of nitrogen, oxygen and sulfur atoms wherein a carbocyclic ring or heterocyclic ring may be condensed to the heterocyclic ring.

6. The process for the production of aldehydes according to claim 2, wherein the substitutents $R^{a1}$ and $R^{a2}$ in the formula (2a) are independently aliphatic hydrocarbon groups having 1 to 15 carbon atoms, alicyclic hydrocarbon groups wherein a carbocyclic ring or heterocyclic ring may be condensed to a nonaromatic carbocyclic ring constituting the alicyclic hydrocarbon groups, aromatic hydrocarbon groups wherein a carbocyclic ring or heterocyclic ring may be condensed to an aromatic ring constituting the aromatic hydrocarbon groups, or heterocyclic groups each having a 5- or 6- membered heterocyclic ring 1 to 3 of at least one heteroatom selected from the group consisting of nitrogen, oxygen and sulfur atoms wherein a carbocyclic ring or heterocyclic ring may be condensed to the heterocyclic ring.

7. The process for the production of aldehydes according to claim 1, wherein the ether represented by the formula (2) is (i) a compound in which $R^a$ is a 1-alkenyl group or (ii) a compound in which $R^a$ and $R^c$ together form, with the adjacent carbon atom and oxygen atom, a nonaromatic heterocyclic ring having about 3 to 20 members, where a carbocyclic ring or heterocyclic ring may be condensed to the nonaromatic heterocyclic ring.

8. The process for the production of aldehydes according to claim 2, wherein the ether represented by the formula (2a) is (i) a compound in which $R^{a1}$ is a 1-alkenyl group or (ii) a compound in which $R^{a1}$ and $R^{a2}$ together form, with the adjacent carbon atom and oxygen atom, a nonaromatic heterocyclic ring having about 3 to 20 members, where a carbocyclic ring or heterocyclic ring may be condensed to the nonaromatic heterocyclic ring.

9. The process for the production of aldehydes according to either of claim 1 or claim 2, wherein $R^1$ and $R^2$ are independently selected from the group consisting of iodine, bromine chlorine, fluorine, methyl, ethyl, propyl, isopropyl, butyl, isobutyl, s-butyl, t-butyl, pentyl, hexyl, heptyl, octyl, decyl, phenyl, naphthyl, cyclopentyl, cyclohexyl, methoxy, ethyoxy, propoxy, isopropoxy, butoxy, isobutoxy, t-butoxy, pentyloxy, hexyloxy, methoxycarbonyl, ethoxycarbonyl, propolxycarbonyl, isopropoxycarbonyl, butoxycarbonyl, pentyloxycarbonyl, hexyloxycarbonyl, formyl, acetyl, propionyl, butyryl, isobutyryl, valeryl, isovaleryl and pivaloyl.

10. The process for the production of aldehydes according to either of claims 1 or 2, wherein the imide of formula (1) is represented by one of formulas (1a)–(1f):

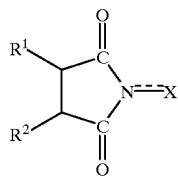
(1a)

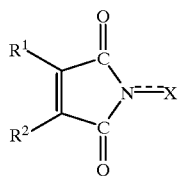
(1b)

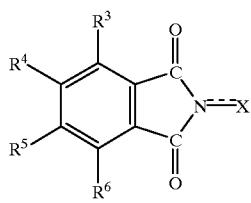
(1c)

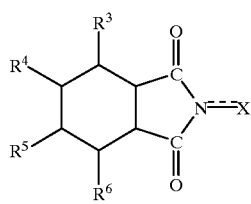
(1d)

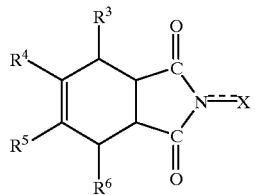
(1e)

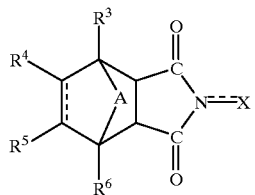
(1f)

wherein each of $R^3$ to $R^6$ is independently selected from the group consisting of a hydrogen atom, an alkyl group, a haloalkyl group, a hydroxyl group, an alkoxy group, a carboxyl group, an alkoxycarbonyl group, an acyl group, a nitro group, a cyano group, an amino group and a halogen atom, and of $R^3$ to $R^6$, adjacent groups may combine to form an aromatic or nonaromatic ring, and A represents a methylene group or an oxygen atom.

11. The process for the production of aldehydes according to either of claims 1 or 2, wherein the amount of the imide of formula (1) is from about 0.001 to 1 mole per mole of the ether.

12. The process for the production of aldehydes according to either of claims 1 or 2, wherein the process is carried out at a temperature of about 0° C. to 300° C.

13. The process for the production of aldehydes according to either of claims 1 or 2, wherein the process is carried out for a time of about 30 minutes to 48 hours.

* * * * *